(12) United States Patent
Palmer

(10) Patent No.: US 10,052,454 B2
(45) Date of Patent: Aug. 21, 2018

(54) CATHETER PACKAGING WITH MOVEMENT CONTROL DEVICE

(71) Applicant: CURE MEDICAL, LLC, Newport Beach, CA (US)

(72) Inventor: Timothy Palmer, Stillwater, MN (US)

(73) Assignee: Cure Medical, LLC, Newport Beach, CA (US)

( * ) Notice: Subject to any disclaimer, the term of this patent is extended or adjusted under 35 U.S.C. 154(b) by 375 days.

(21) Appl. No.: 15/067,717

(22) Filed: Mar. 11, 2016

(65) Prior Publication Data

US 2016/0193443 A1 Jul. 7, 2016

Related U.S. Application Data

(63) Continuation-in-part of application No. 14/296,995, filed on Jun. 5, 2014, now Pat. No. 9,782,563.

(51) Int. Cl.
*A61M 25/00* (2006.01)
*A61M 27/00* (2006.01)

(52) U.S. Cl.
CPC ...... *A61M 25/002* (2013.01); *A61M 25/0017* (2013.01); *A61M 2202/0496* (2013.01); *A61M 2209/06* (2013.01)

(58) Field of Classification Search
CPC ............ A61M 2209/06; A61M 25/002; A61M 25/0017; A61M 27/00
USPC .................................. 604/328, 327, 540–544
See application file for complete search history.

(56) References Cited

U.S. PATENT DOCUMENTS

| 1,206,655 | A | | 11/1916 | Belcher |
| 2,131,956 | A | | 7/1937 | Jones |
| 2,221,801 | A | | 3/1938 | Keppinger |
| 2,422,891 | A | | 9/1945 | Dickson |
| 2,584,644 | A | | 9/1950 | Verdi |
| 2,894,119 | A | | 9/1957 | Stenger |
| 3,365,761 | A | | 10/1965 | Kalvig |
| 4,141,452 | A | | 2/1979 | Martin et al. |
| 4,230,115 | A | | 10/1980 | Walz, Jr. et al. |
| 5,108,066 | A | * | 4/1992 | Lundstrom ........ A63B 21/0728 24/524 |
| D358,679 | S | | 5/1995 | Garrity |
| 5,454,798 | A | | 10/1995 | Kubalak et al. |
| 6,010,105 | A | | 1/2000 | Davis |
| 6,053,905 | A | | 4/2000 | Daignault, Jr. et al. |

(Continued)

*Primary Examiner* — Susan Su
(74) *Attorney, Agent, or Firm* — Sherrill Law Offices, PLLC

(57) ABSTRACT

Flexible packaging with an integrated component for controlled dispensing of a flexible elongate tubular product, such as a catheter, retained within the packaging. The dispensing control device is disposed at one end of the packaging and includes a housing and a locking member. The housing member is attached to one end of the packaging and provides a linear exit passageway through the packaging. The locking member is hingedly attached to the housing within the product retention chamber, and has an orifice that extends through the locking member. The locking member is pivotable relative to the housing as between a first dispensing position wherein the central axis of the orifice is aligned with the central axis of the passageway, and a second locked position wherein the central axis of the orifice is misaligned with the central axis of the pathway through the housing.

10 Claims, 13 Drawing Sheets

(56) References Cited

U.S. PATENT DOCUMENTS

| | | | |
|---|---|---|---|
| 6,402,726 B1 | 6/2002 | Genese | |
| 6,578,709 B1 | 6/2003 | Kavanagh et al. | |
| 6,602,244 B2* | 8/2003 | Kavanagh | A61M 25/002 604/172 |
| 7,458,964 B2 | 12/2008 | Mosler et al. | |
| 9,011,413 B2* | 4/2015 | Chung | A61M 25/0017 604/528 |
| 2007/0073222 A1 | 3/2007 | Lilley, Jr. et al. | |
| 2008/0103464 A1 | 5/2008 | Mosler et al. | |
| 2010/0312227 A1* | 12/2010 | House | A61M 25/0017 604/544 |
| 2011/0098682 A1* | 4/2011 | Ahmed | A61M 25/04 604/544 |
| 2013/0110087 A1* | 5/2013 | Kane | A61M 25/00 604/543 |
| 2014/0276661 A1* | 9/2014 | Hannon | A61M 25/0069 604/544 |
| 2015/0352321 A1* | 12/2015 | Hannon | A61M 25/0067 604/544 |

* cited by examiner

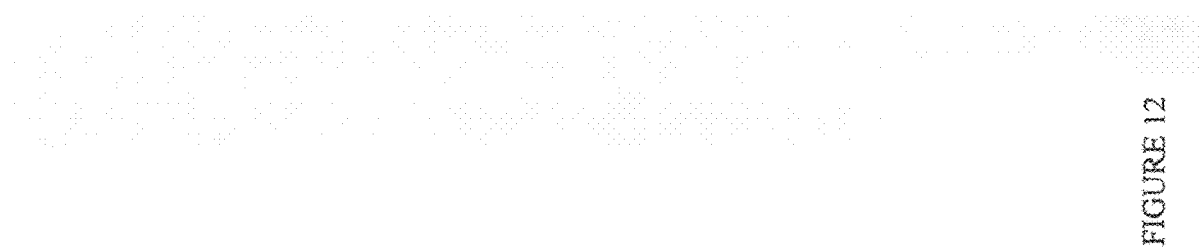
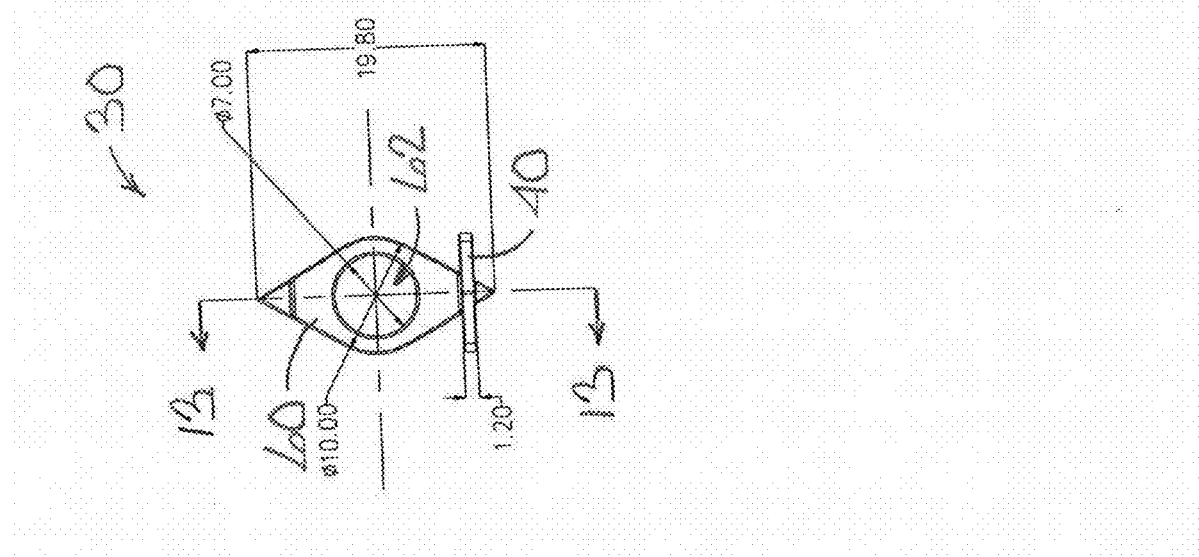
FIGURE 12

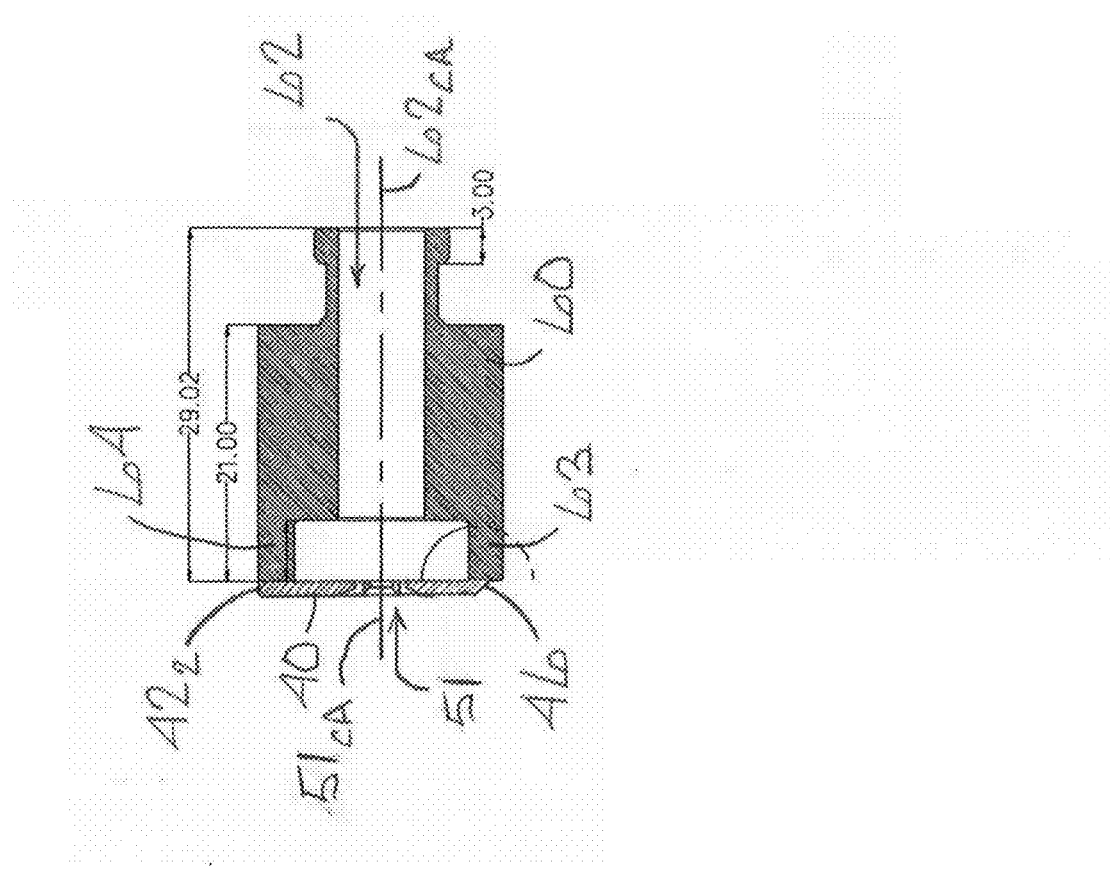

CATHETER PACKAGING WITH MOVEMENT CONTROL DEVICE

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need single use catheters have been developed to allow patients to perform self catheterization. To aid in the insertion of the catheter in a body cavity they are often lubricated making the handling of the catheter difficult and messy. Many catheter packages are now designed to aid in the use of the catheter and at least the funnel end of the catheter is retained in the package. This allows the user to use the package to manipulate the catheter and avoid the messy and possible insanitary handling of the actual catheter. Manipulating a slippery catheter through a plastic bag can be quite difficult even for someone with excellent dexterity. To aid in the manipulation of the catheter various devices have been conceived to limit or control the movement of the catheter into and out of its package.

Many of these movement control devices have multiple parts increasing cost, weight, and waste of the overall catheter and packaging.

Therefore, a need exists for a low cost, lightweight, and low waste catheter movement control device.

SUMMARY OF THE INVENTION

A first aspect of the invention is an intermittent urinary catheter packaging having a longitudinally extending package and a catheter movement control device. The catheter movement control device is disposed within the package and has a monolithic planar locking member and a one-way valve. The monolithic locking member has longitudinally spaced upper and lower surfaces, laterally spaced ends, and transversely spaced front and back edges. The valve is disposed through the upper and lower surfaces of the locking member and configured and arranged for receipt of the catheter tube and to advance the tube through the locking member in the first longitudinal direction only.

A second aspect of the invention is flexible packaging with an integrated component for controlled dispensing of a flexible elongate tubular product retained within the packaging. The dispensing control device is disposed at one end of the packaging and includes a housing and a locking member. The housing member is attached to one end of the packaging and provides a linear exit passageway through the packaging. The locking member is hingedly attached to the housing within the product retention chamber, and has an orifice that extends through the locking member. The locking member is pivotable relative to the housing as between a first position wherein the central axis of the orifice is aligned with the central axis of the passageway, and a second position wherein the central axis of the orifice is misaligned with the central axis of the pathway through the housing.

A third aspect of the invention is a packaged intermittent urinary catheter that includes an intermittent urinary catheter, packaging retaining the intermittent urinary catheter, and a catheter movement control device. The catheter movement control device is disposed at one end of the packaging and includes a housing and a locking member. The housing is attached to one end of the packaging and has (~) longitudinally spaced opposed first and second ends with the first end disposed outside the receiving chamber and the second end disposed inside the receiving chamber, (~) a pathway extending through the housing between the first and second ends defining an exit port through which the catheter retained within the receiving chamber of the packaging may be withdrawn from the packaging, and (~) a pair of laterally spaced tabs extending longitudinally from the second end of the housing, positioned on diametric sides of the pathway. The locking member has (~) an orifice located between first and second ends of the locking member, configured and arranged to frictionally engage the catheter so as to accommodate passage of the catheter through the orifice when the catheter is axially aligned with the orifice, while inhibiting passage of the catheter through the orifice when the catheter is axially misaligned with the orifice, and (~) a hinge connecting the first end of the locking member to a distal end of one of the tabs for allowing pivoting of the locking member relative to the housing upon axial movement of the catheter when frictionally engaged within the orifice of the locking member as between a first position wherein the second end of the locking member contacts the distal end of the other tab and the central axis of the orifice through the locking member aligns with the central axis of the pathway through the housing, and a second position wherein the second end of the locking member is spaced from the distal end of the other tab and the central axis of the locking member is misaligned with the central axis of the pathway through the housing. Such pivoting of the locking member permits withdrawal of the catheter from the packaging through the passageway in the housing, while inhibiting return of a withdrawn length of the catheter into the packaging.

BRIEF DESCRIPTION OF THE DRAWINGS

FIG. 12 is an end view of the catheter movement control device depicted in FIG. 10 with dimensions for a particular embodiment set forth in mm.

FIG. 14 is a cross-sectional side view of the catheter movement control device depicted in FIG. 13 with the locking mechanism pivoted into the first dispensing position.

DETAILED DESCRIPTION OF A PREFERRED EMBODIMENT

Figure 1:
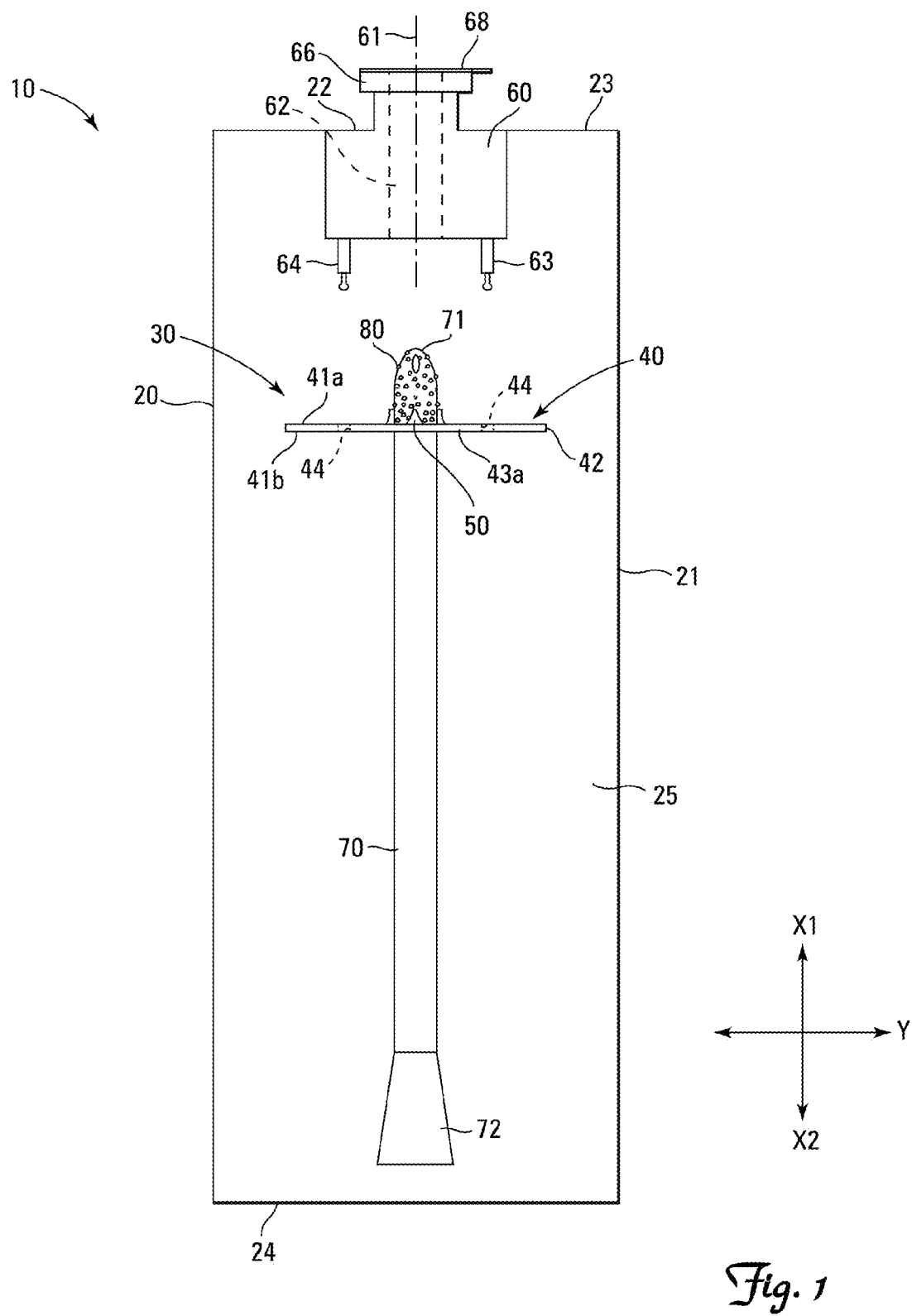
FIG. 1 is a front plan view of the invention with a first embodiment of the movement control device.

Nomenclature
10 Catheter Packaging
20 Package
21 Longitudinally Extending Side
22 Exit
23 First Longitudinal End
24 Second Longitudinal End
25 Receiving Chamber
26 Line of Weakness
30 Movement Control Device
40 Monolithic Planar Locking Member
41a Upper Surface
41b Lower Surface
42 Lateral End
421 First or One Lateral End of Locking Member
422 Second or Other Lateral End of Locking Member
43a Front Edge
43b Back Edge
44 Locking Orifice
45 Snap Fit Latch
46 Hinge
50 Valve
51 Valve Orifice
$51_{CA}$ Central Axis of Valve Orifice
60 Housing
61 Longitudinal Axis
62 Pathway
$62_{CA}$ Central Axis of Pathway
63 First Longitudinally Extending Engagement Member
64 Second Longitudinally Extending Engagement Member
65 Slots or Catches
66 First Longitudinal End
67 Second Longitudinal End
68 Cap or Seal
70 Catheter
71 Lumen End
72 Funnel End
80 Lubricant
X1 First Longitudinal Direction
X2 Second Longitudinal Direction
Y Lateral Direction
Z Transverse Direction

DESCRIPTION

Construction

The invention is catheter packaging 10 with a package 20 and a catheter movement control device 30. The package 20 has a first longitudinal end 23 and a second longitudinal end 24 and defines a longitudinally elongate catheter receiving chamber 25 extending along a portion of the full longitudinal length of the package 20 configured to contain at least part of a catheter 70. Preferably the entire catheter 70 is carried in the elongate receiving chamber 25 with the lumen end 71 of the catheter 70 located proximate the first longitudinal end 23 of the package 20 and the funnel end 72 proximate the second longitudinal end 24 of the package 20.

As shown in FIG. 1, a preferred embodiment of the package 20 may be constructed from a base sheet of material and cover sheet of material sealed along the edges to form the catheter receiving chamber 25 therein. The first longitudinal end 23 and the second longitudinal end 24 are sealed after insertion of the catheter 70 and movement control device 30 in the receiving chamber 25. A second embodiment of the package 20 may also be constructed from a single base material folded upon it to provide a single sealed longitudinal edge. The first longitudinal end 23 and second longitudinal end 24 are then sealed after insertion of the catheter 70 and movement control device 30 in the receiving chamber 25. In a third embodiment the package 20 may be extruded in a tube shape and then the first longitudinal end 23 and second longitudinal end 24 sealed after insertion of the catheter 70 and movement control device 30 in the receiving chamber 25.

The catheter 70 inserted in the package 20 is an intermittent catheter 70. The catheter 70 may be coated with a hydrophilic coating to provide a low friction surface when treated with a swelling medium. A swelling medium may be provided within the package 20 to provide a ready to use catheter 70. A lubricant 80 may also be provided in the package 20 to provide a low friction surface.

The catheter 70 may have any desired longitudinal length and shape effective for achieving the function of eliminating urine from the bladder of a male or female patient. Preferably, the longitudinal length for an adult female catheter 70 is between 2-6 inches, the longitudinal length of the adult male catheter 70 is between 10-16 inches, and the longitudinal length of a pediatric catheter 70 is between 5-11 inches.

The catheter receiving chamber 25 also contains within it a catheter movement control device 30. The catheter movement control device 30 has a monolithic planar locking member 40 and a one-way valve 50. The locking member 40 has longitudinally spaced upper and lower surfaces 41a and 41b, laterally spaced ends 42, and transversely spaced front and back edges 43a and 43b. The locking member 40 may be made from any suitable thin and lightweight material. Preferably the locking member 40 is made of a heavy flexible polyvinyl chloride (PVC) film.

The locking member 40 has a one-way valve 50 disposed through the upper and lower surfaces 41a and 41b of the locking member 40 as shown in FIGS. 1, 4, 6A, and 9 to allow movement of the catheter 70 through the locking member 40 in the first longitudinal direction X1 but not the second longitudinal direction X2. Any type of one way valve 50 may be utilized. Preferably a tricuspid or quadricuspid valve 50 is used. The valve 50 is sized and shaped to allow the catheter70 to move freely through the locking member 40 in the first longitudinal direction X1 and not the second longitudinal direction X2.

The catheter movement control device 30 may also have a catheter housing 60. The housing 60 has a first longitudinal end 66 and a second longitudinal end 67. Preferably the housing 60 is attached to at least one of the longitudinally extending sides 21 of the package 20. Most preferably the housing 60 is positioned within the exit 22 to the package 20 as shown in FIG. 1 with the first longitudinal end 66 of the housing 60 allowing the catheter 70 to exit from the package 20 and the second longitudinal end 67 of the housing 60 within the receiving chamber 25. The housing 60 has a longitudinal axis 61 and defines a longitudinally extending pathway 62 through the housing 60. The pathway 62 is sized and configured for receipt of the catheter 70. The housing 60 is disposed a longitudinal distance from the valve 50 in the first longitudinal direction X1. The housing 60 may also be disposed a longitudinal distance for the first longitudinal end 23 of the package 20.

Figure 5:
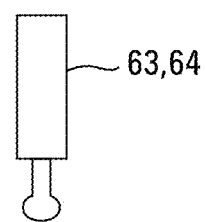
FIG. 5 is an enlarged front plan view of the longitudinally extending posts shown in FIG. 3.

In a second embodiment of the housing 60, the housing 60 has one or two longitudinally extending and laterally spaced engagement members 63 and 64 extending in the second longitudinal direction X2 from the second longitudinal end 67 of the housing 60. See FIGS. 1-3. The engagement member may be any shape and size to allow engagement with corresponding locking orifices 44 disposed through the upper and lower surfaces 41a and 41b of the locking member 40 shown in FIG. 4. Preferably the engagement members 63 and 64 are post shaped members 63 and 64 as shown in FIG. 5. Preferably the housing 60 is made from a lightweight plastic.

Figure 7:
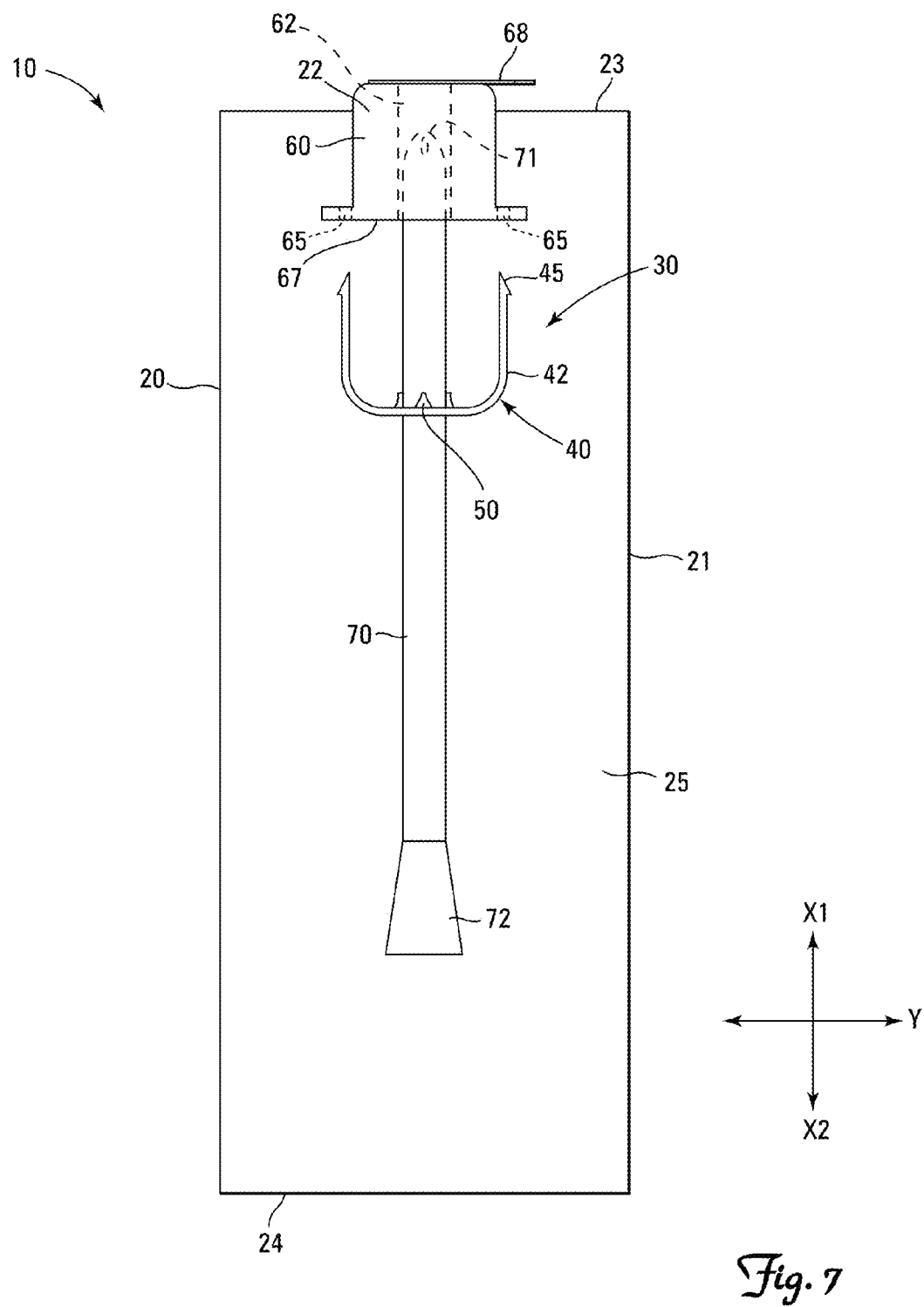
FIG. 7 is a front plan view of a third embodiment of the catheter movement control device in the package.
Figure 8:
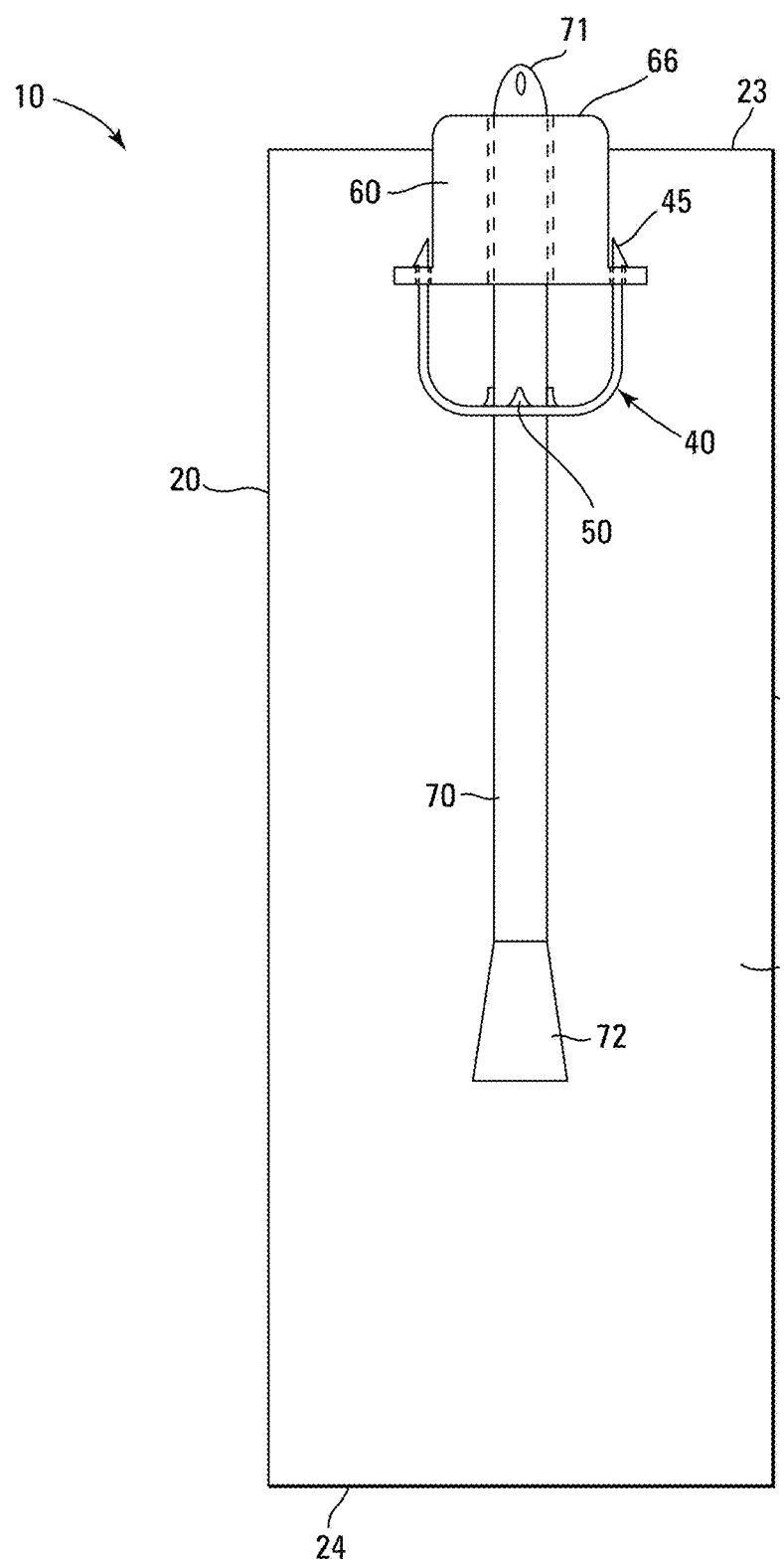
FIG. 8 is a front plan view of the catheter movement control device in FIG. 7 with the movement control device engaging the housing to prevent movement in the second longitudinal direction.

In a third embodiment of the housing 60, the housing 60 has two laterally spaced slots or catches 65 in the second longitudinal end 67 configured and arranged to snap fit with the locking member 40. In this embodiment the locking member 40 has a snap fit latch 45 extending in the first longitudinal direction X1 on the first and second lateral ends 42 as shown in FIGS. 7 and 8. The snap fit latches 45 are configured and arranged to deflect and snap into the slot or catch 65 of the housing 60 to prevent movement of the locking member 40 in the second longitudinal direction X2.

Figure 6:
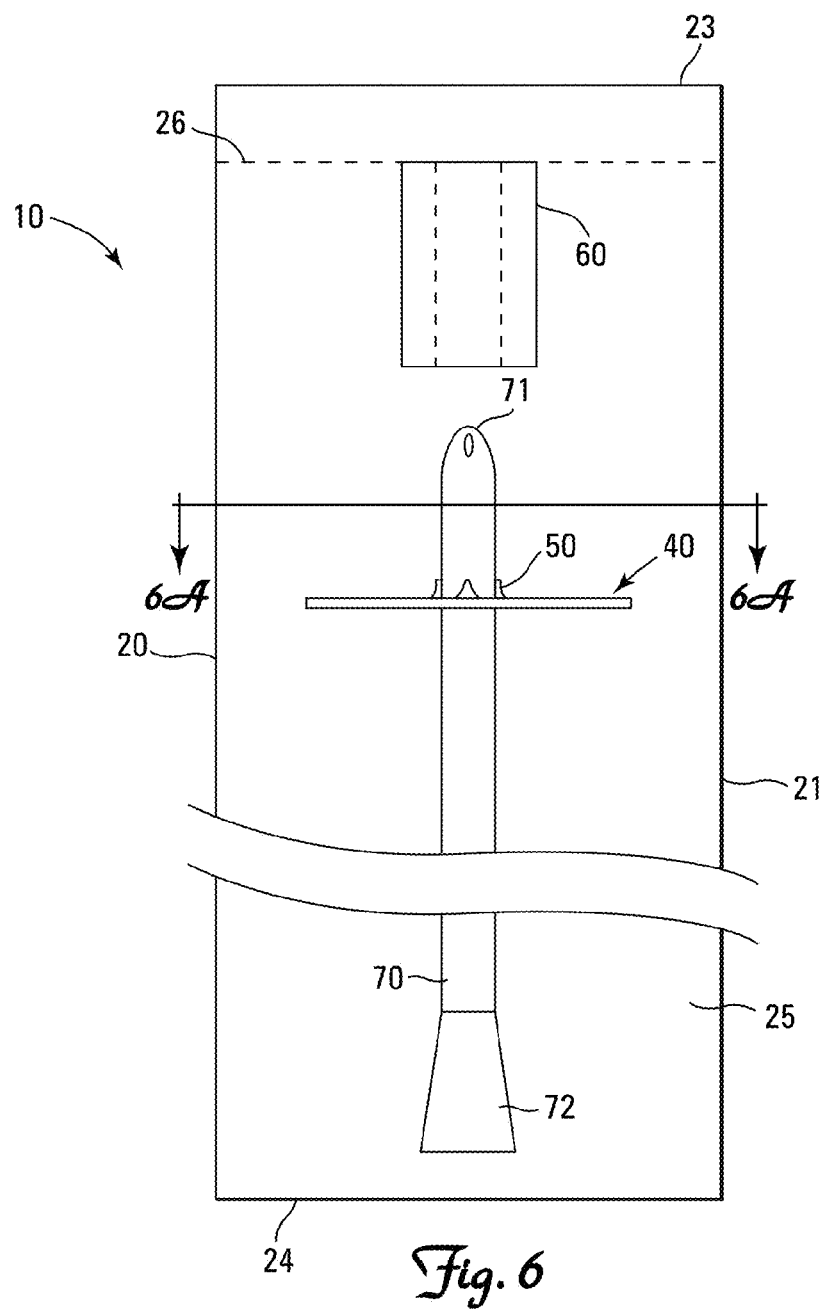
FIG. 6 is a front plan view of a second embodiment of the movement control device.
Figure 6A:
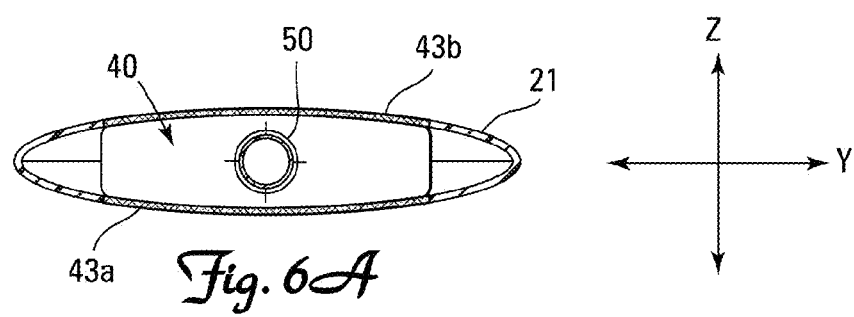
FIG. 6a is top view of the catheter movement control device along the line A-A of FIG. 6 wherein the transversely spaced front and back edges are attached to the longitudinal sides of the package.
Figure 9:
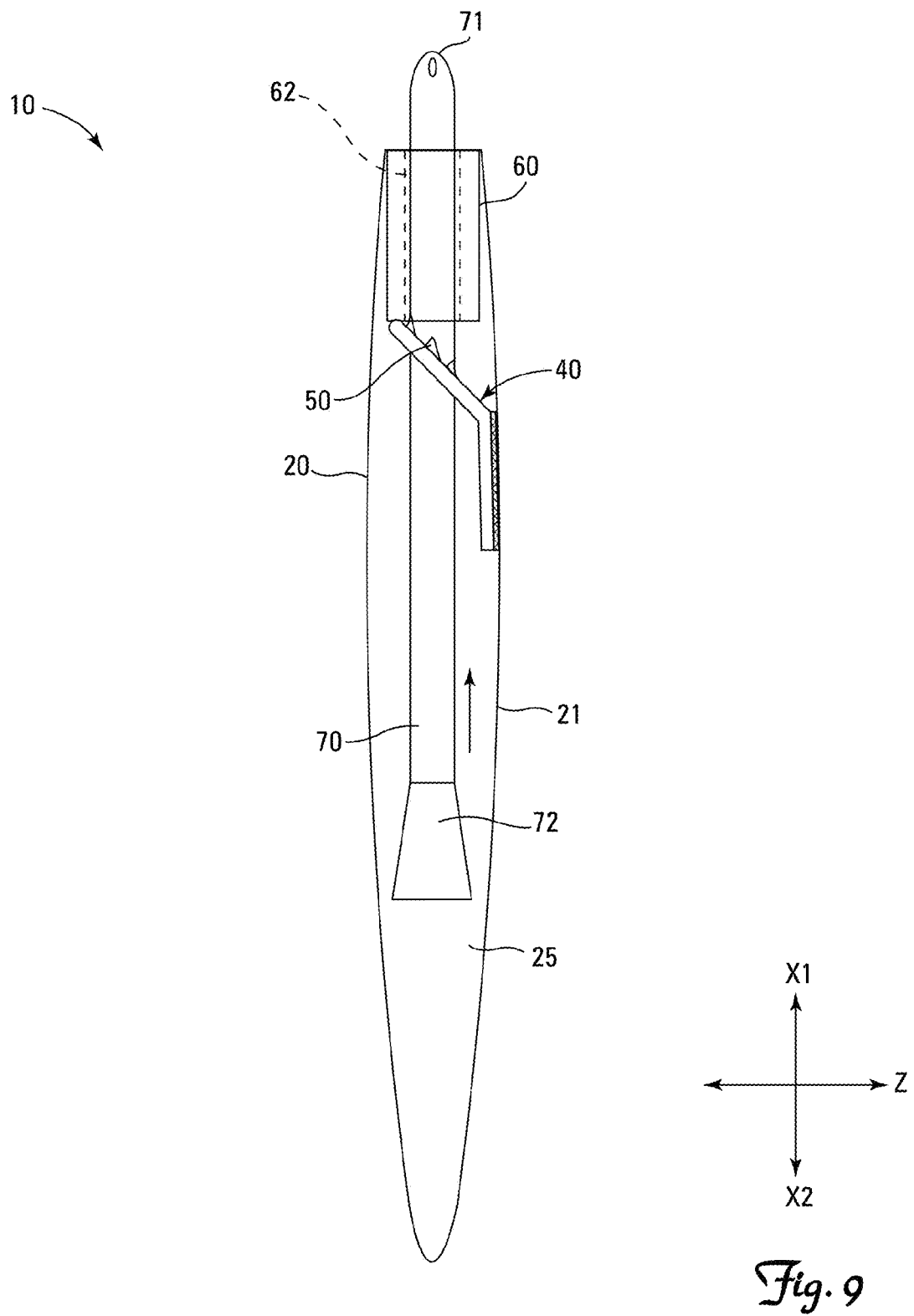
FIG. 9 is a side plan view of a fourth embodiment of the catheter movement control device with a back edge hingedly attached to a longitudinal side of the package.
Figure 10:
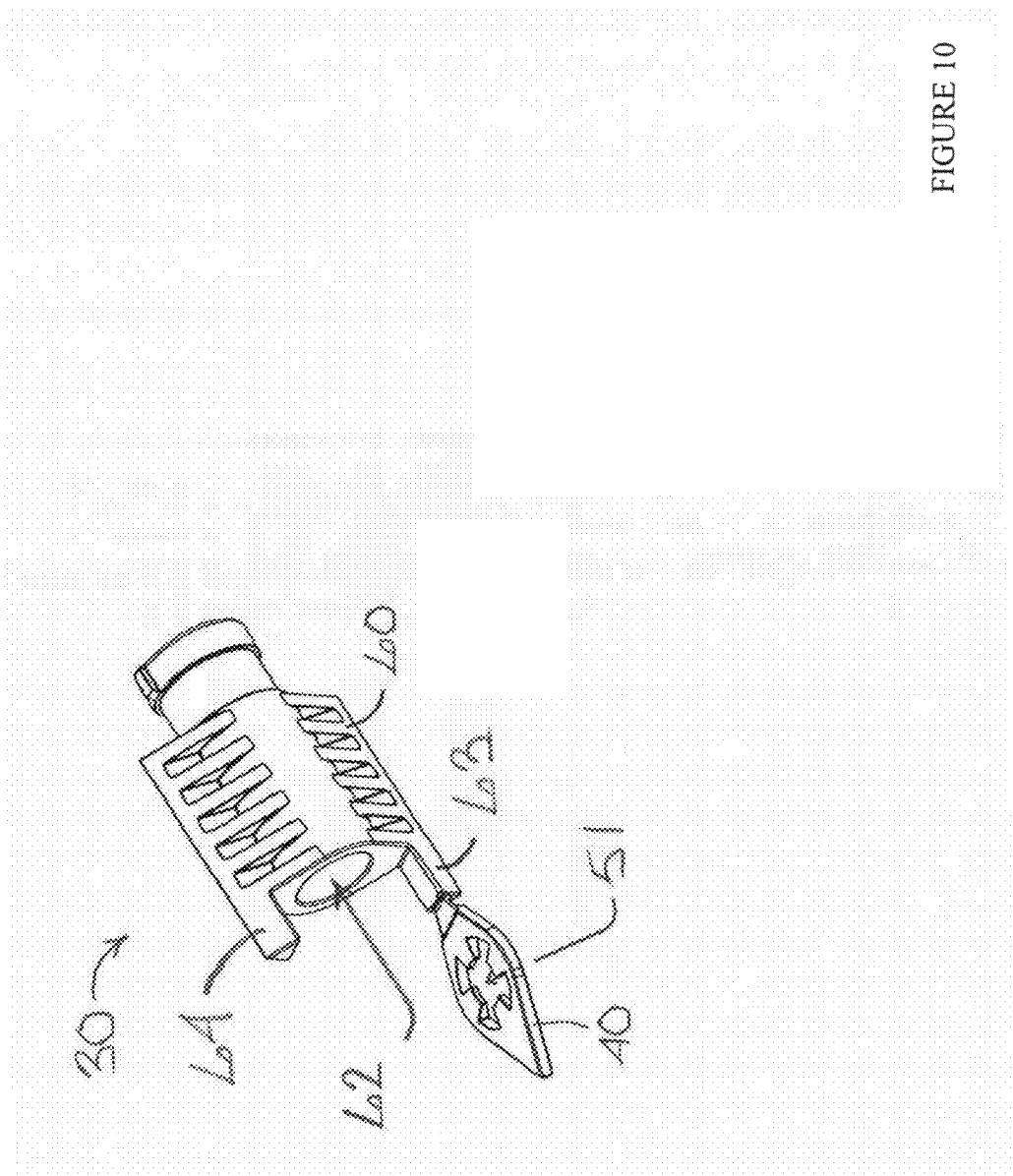
FIG. 10 is a perspective view of a fifth embodiment of the catheter movement control device with the locking mechanism pivoted into a second locking position.
Figure 11:
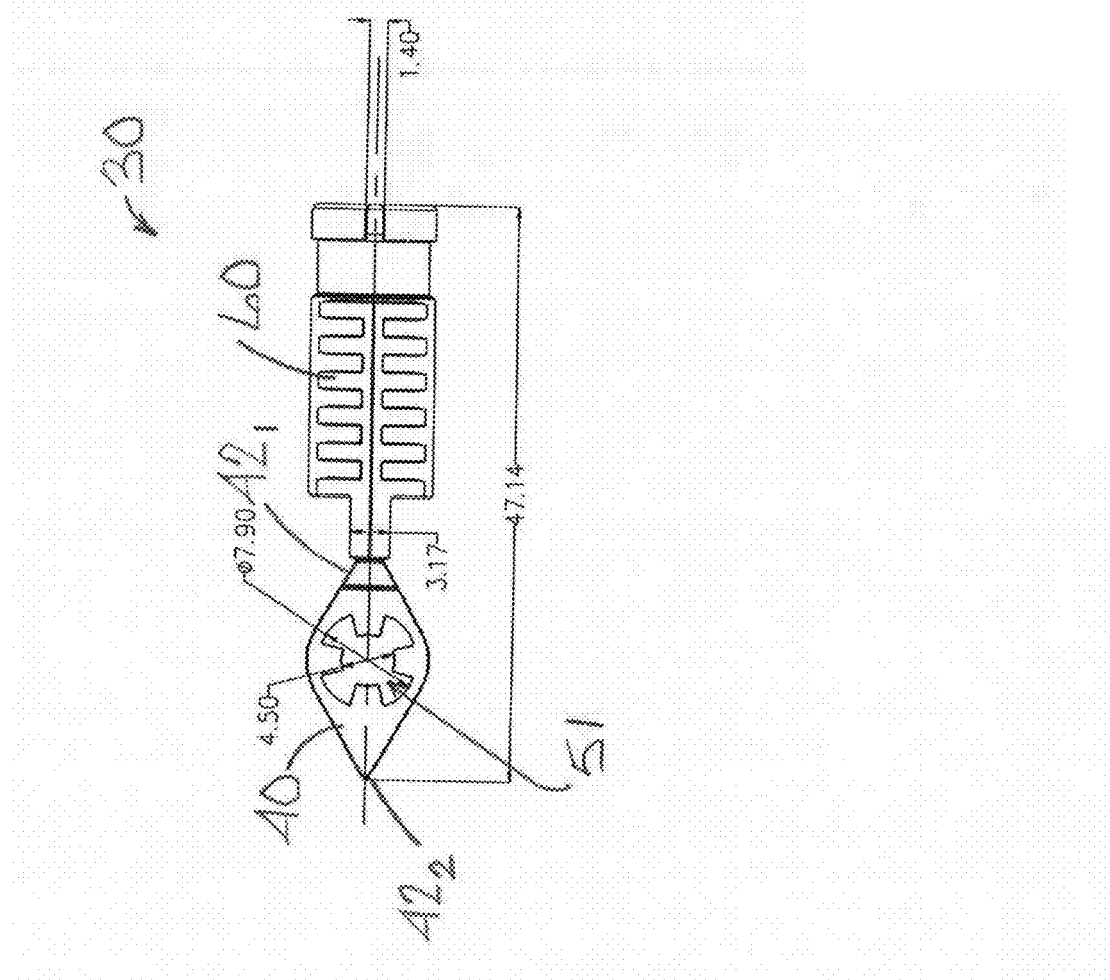
FIG. 11 is a side view of the catheter movement control device depicted in FIG. 10 with dimensions for a particular embodiment set forth in mm.
Figure 13:
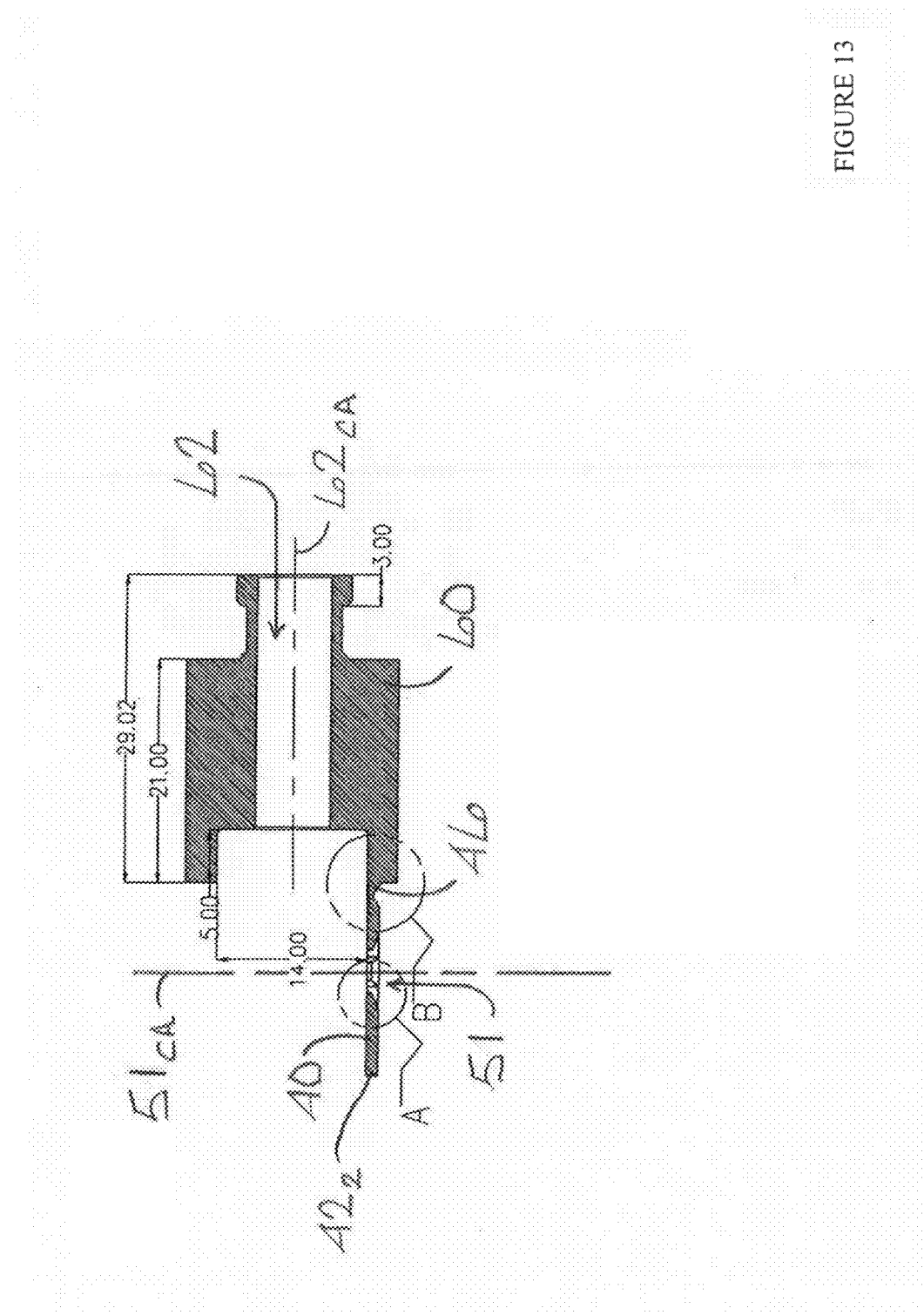
FIG. 13 is a cross-sectional side view of the catheter movement control device depicted in FIG. 12 taken along line 13-13 and with dimensions for a particular embodiment set forth in mm.

The monolithic planar locking member 40 may also be attached to a longitudinally extending side 21 of the package 20. Either the lateral ends 42 or the front and back edges 43a and 43b can be attached to the package 20. As shown in FIGS. 6 and 6A, the transversely spaced front and back edges 43a and 43b of the locking member 40 may be welded to the package 20 to prevent the locking member 40 from moving in the longitudinal direction relative to the package 20. As shown in FIG. 9, either the front edge 43a or back edge 43b may be hingedly attached to the package 20.

Use

The packaged intermittent urinary catheter 10 is used by patients for self catheterization. Prior to use the patient should take all sanitary procedures advised by their doctors to decrease the risks of infection from utilizing a catheter 10.

No Housing

In the embodiment of the invention shown in FIG. 6, the package 20 has no housing 60 at the first longitudinal end 23. To open the package 20 to access the catheter 70, the patient grasps the first longitudinal end 23 of the package 20 and removes the end 23. The end 23 may be removed by cutting with a knife or scissors, but preferably the end 23 is removed manually along a line of weakness 26. By removing the first longitudinal end 23 at the point of weakness or line of weakness 26, the package 20 will open such that the receiving chamber 25 is now open.

The second longitudinal end 24 of the package 20 may also be removed to allow the package 20 to be used as an extended drainage tube or left intact so that the package 20 can be used as collection vessel. The second longitudinal end 24 may be removed by cutting with a knife or scissors, but preferably the end 24 is removed manually along a line or point of weakness 26.

Both the front edge 43a and back edge 43b of the locking member 40 are attached or fused to the longitudinally extending sides 21 of the package 20 preventing any longitudinal movement of the locking member 40. The user grasps the catheter 70 below the locking member 40 (near the funnel end 72) and urges the catheter 70 in the first longitudinal direction X1 through the locking member 40 until the lumen end 71 of the catheter 70 advances out of the package 20. The catheter 70 continues to be advanced out of the package 20 and into the urethra of the user. If the catheter 70 encounters resistance advancing in the first longitudinal direction X1, the one-way valve 50 in the locking member 40 grabs the catheter 70 and prevents it from moving in the second longitudinal direction X2.

Housing

If the package 20 has a housing 60 located within the exit 22 of the package 20, a seal or cap 68 covers the opening out of the housing 60. See FIGS. 1, 2 and 7. The seal or cap 68 is removed to open the pathway 62 through the housing 60 and catheter receiving chamber 25.

Locking Member Attached to Package

In the embodiment of the invention shown in FIG. 9, the movement control device 30 includes a housing 60. Only one edge of the locking member 40 is attached to a longitudinally extending side 21 of the package 20. Preferably this attached edge is hingedly attached. This allows the other edge to move in both the first longitudinal direction X1 and the second longitudinal direction X2. The user grasps the catheter 70 below the locking member 40 (near the funnel end 72) and urges the catheter 70 in the first longitudinal direction X1 through the locking member 40 until the lumen end 71 of the catheter 70 advances out of the package 20. The catheter 70 continues to be advanced through the pathway 62 of the housing 60 and out of the package 20 and into the urethra of the user. If the catheter 70 encounters resistance advancing in the first longitudinal direction X1, the one-way valve 50 in the locking member 40 grabs the catheter 70 and prevents it from moving in the second longitudinal direction X2. As the catheter 70 is advanced, the unattached edge of the locking member 40 moves with the catheter 70 until it comes into contact with the housing 60. This contact prevents the unattached edge of the locking member 40 from continuing to advance in the first direction and preventing movement in the first longitudinal direction X1 of the catheter 70 through the one way valve 50. The lumen end 71 of the catheter 70 is advanced through the pathway 62 through the housing 60 and out of the package 20.

Locking Member Attached To Housing

In the embodiment of the invention shown in FIGS. 1-3, 7-8 and 10-13 the user grasps the catheter 70 through the package 20 below the locking member 40 and manually urges the catheter 70 in the first longitudinal direction X1 toward the housing 60. As the lumen end 71 of the catheter 70 moves toward the housing 60, the locking member 40 also advances toward the housing 60. The lumen end 71 of the catheter 70 is urged into the pathway 62 of the housing 60 and the upper surface 41a of the locking member 40 is urged into contact with the second longitudinal end 67 of the housing 60.

Figure 2:
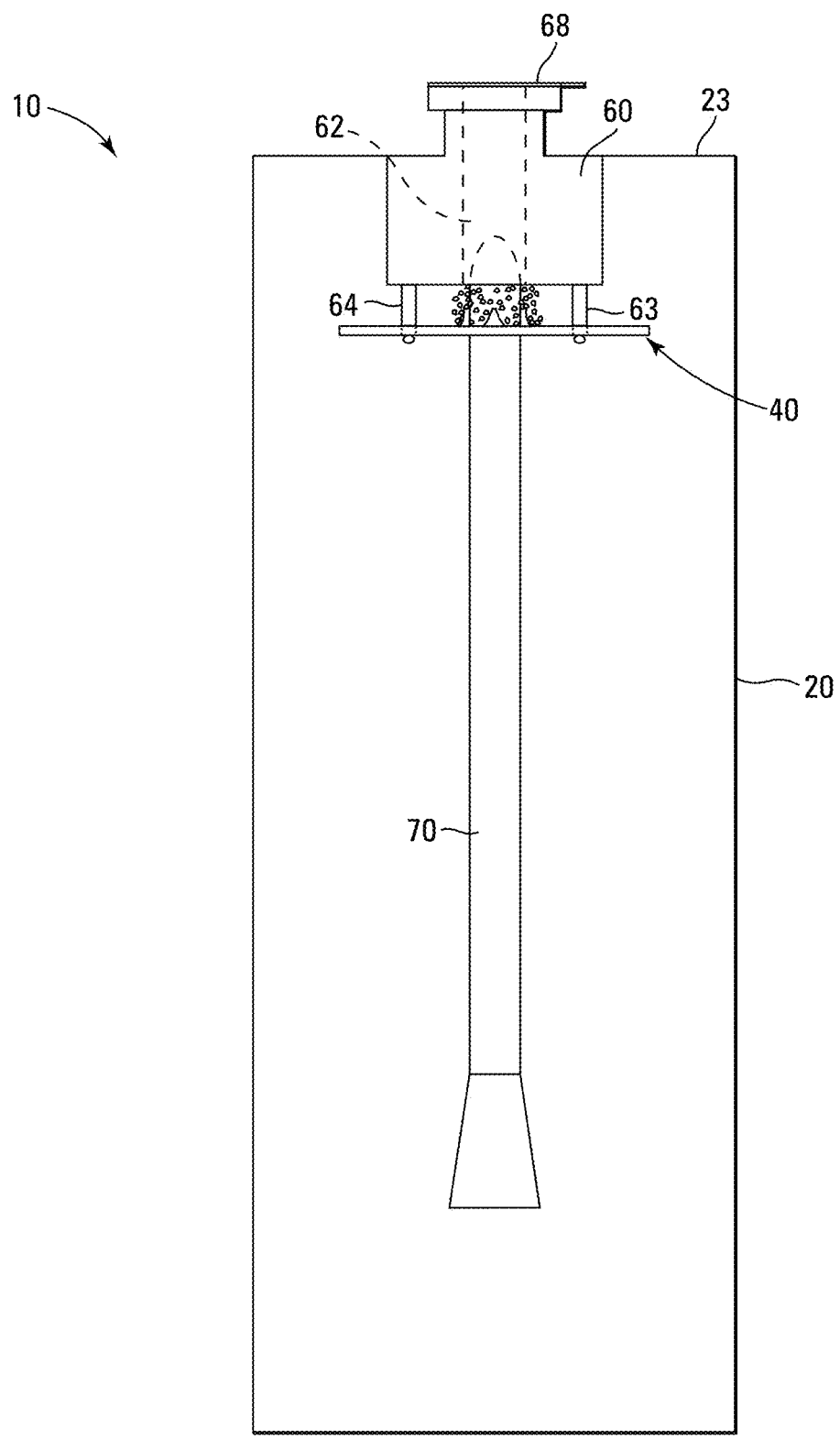
FIG. 2 is a front plan view of the invention in FIG. 1 shown with the catheter moving in the first longitudinal direction as the user advances the catheter into the exit of the package.
Figure 3:
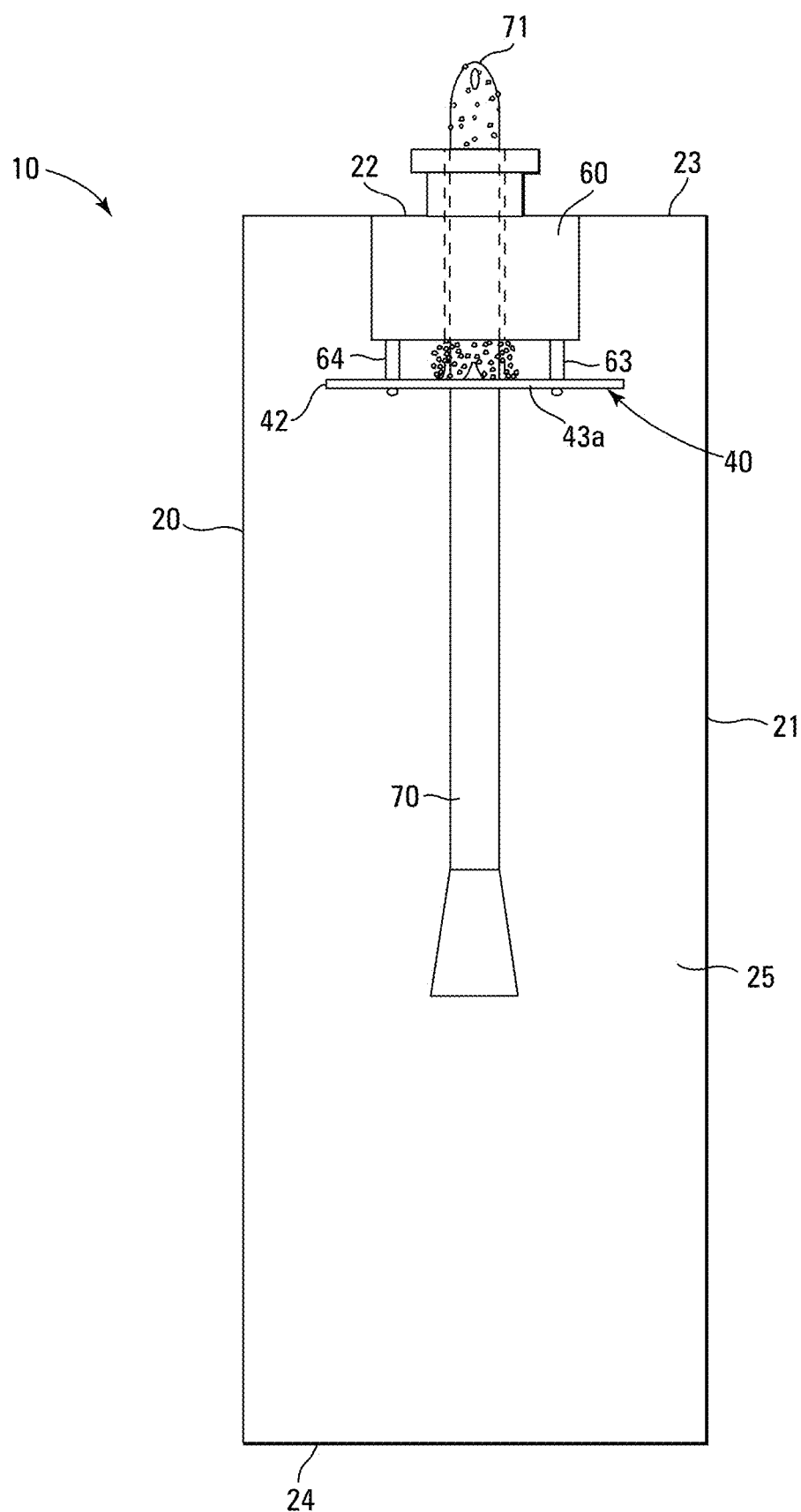
FIG. 3 is a front plan view of the invention in FIG. 3 with the movement control device engaging the housing to prevent movement in the second longitudinal direction.
Figure 4:
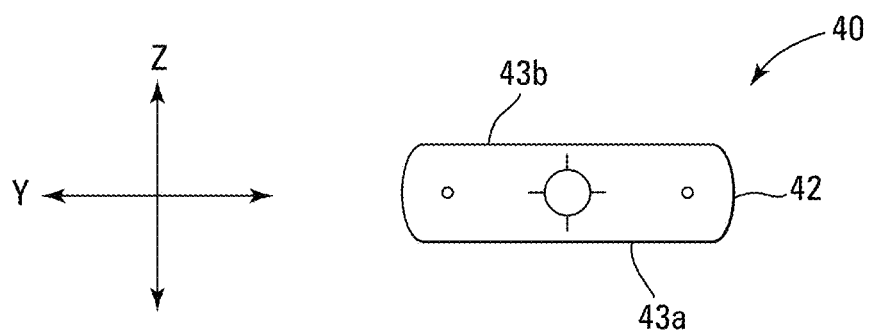
FIG. 4 is a top plan view of the monolithic planar locking member shown in FIG. 1.

In the embodiment of the invention shown in FIGS. 1-3, the housing 60 has first and second longitudinally extending engagement members 63 and 64 extending in the second longitudinal direction X2 from the housing 60. The engagement members 63 and 64 snap fit into locking orifices 44 in the locking member 40 preventing the locking member 40 from moving out of contact with the housing 60 member. In the embodiment of the invention shown in FIGS. 7 and 8, the housing 60 has slots or catches 65 in the second longitudinal end 67. The locking member 40 has snap fit latches 45 extending in the first longitudinal direction X1 on the first and second lateral ends 42 that are configured and arranged to mate with the slots or catches 65 in the housing 60. In both embodiments the catheter 70 and the locking member 40 are advanced in the first longitudinal direction X1. The lumen end 71 of the catheter 70 enters the pathway 62 to advance out of the package 20 and the locking member 40 snap fits into place with the housing 60.

Once the locking member 40 has snap fit into place with the housing 60, the locking member 40 can no longer move in the second longitudinal direction X2. The catheter 70 continues to advance out of the package 20 and into the urethra of the user. As the catheter 70 is advanced if it encounters resistance advancing in the first longitudinal direction X1, the one-way valve 50 in the locking member 40 grabs the catheter 70 and prevents it from moving in the second longitudinal direction X2.

In the embodiment of the invention shown in FIGS. 10-13, engagement members 63 and 64 extend in the second longitudinal direction X2 from the housing 60. One end $42_1$ of the locking member 40 is pivotally attached via a hinge 46, such as a live hinge, to the distal end of one of the engagement members 63 for pivoting as between a first dispensing position, depicted in FIG. 14 and a second locking position depicted in FIG. 13. In the first position, achieved by movement of a catheter 70 passing through the valve orifice 51 towards the housing 60, the other end $42_2$ of the locking member 40 contacts the distal end of the other engagement member 64 whereby the central axis $51_{CA}$ of the valve orifice 51 aligns with the central axis $62_{CA}$ of the pathway 62 through the housing 60. In this configuration the catheter 70 can translate through the valve orifice 54 and can therefore be dispensed out of the packaging 20. In the second position, achieved by movement of a catheter 70 passing through the valve orifice 51 away from the housing 60, the other end $42_2$ of the locking member 40 is pivoted away from the distal end of the other engagement member 64 whereby the central axis $51_{CA}$ of the valve orifice 51 is misaligned with the central axis $62_{CA}$ of the pathway 62 through the housing 60. In this configuration the catheter 70 cannot translate through the valve orifice 51 thereby preventing reinsertion of catheter 70 back into the packaging 20.

In all of the embodiments, the locking member 40 prevents the funnel end 72 of the catheter 70 from advancing out of the package 20. This allows the package 20 to be used as a drainage vessel or an extended drainage tube if the second longitudinal end 24 of the package 20 was removed. It also allows the user to manipulate the catheter 70 without touching the catheter 70. This helps to prevent contamination of the catheter 70 and reduces the mess to the hands of the user.

I claim:

1. Packaging with an integrated component for controlled dispensing of a flexible elongate tubular product retained within the packaging, comprising:
   (a) flexible packaging defining a product retention chamber, and
   (b) a dispensing control device disposed at one end of the packaging, the dispensing control device including at least:
      (i) a housing attached to one end of the packaging and providing a linear exit passageway through the packaging, and
      (ii) a locking member hingedly attached to the housing within the product retention chamber and having an orifice through the locking member,
      (iii) wherein each of the passageway and the orifice define a central axis, and the locking member is pivotable relative to the housing as between a first position wherein the central axis of the orifice is aligned with the central axis of the passageway, and a second position wherein the central axis of the orifice is misaligned with the central axis of the pathway through the housing.

2. The packaging of claim 1 further comprising an intermittent urinary catheter retained within the package.

3. The packaging of claim 1 wherein the locking member is planar.

4. The packaging of claim 1 wherein the locking member is hingedly attached to the housing by a live hinge.

5. The packaging of claim 1 wherein the orifice includes a plurality of inwardly projecting teeth.

6. A packaged intermittent urinary catheter, comprising:
   (a) an intermittent urinary catheter defining a central axis,
   (b) packaging retaining the intermittent urinary catheter in a receiving chamber, and
   (c) a catheter movement control device disposed at one end of the packaging, the catheter movement control device including at least:
      (i) a housing attached to one end of the packaging, the housing having:
         (1) longitudinally spaced opposed first and second ends with the first end disposed outside the receiving chamber and the second end disposed inside the receiving chamber,
         (2) a pathway through the housing extending between an opening in the first end and an opening in second end of the housing, and defining an exit port through which the catheter retained within the receiving chamber of the packaging may be withdrawn from the packaging, and
         (3) a pair of laterally spaced tabs extending longitudinally from the second end of the housing, positioned on diametric sides of the opening in the second end of the housing, and
      (ii) a locking member having:
         (1) laterally opposed first and second ends,
         (2) an orifice defining a central axis located between the first and second ends of the locking member, the orifice configured and arranged to frictionally engage the catheter so as to accommodate passage of the catheter through the orifice when the catheter is axially aligned with the orifice, while inhibiting passage of the catheter through the orifice when the catheter is axially misaligned with the orifice,
         (3) a hinge connecting the first end of the locking member to a distal end of one of the tabs for allowing pivoting of the locking member relative to the housing upon axial movement of the catheter when frictionally engaged within the orifice of the locking member as between a first position wherein the second end of the locking member contacts the distal end of the other tab and the central axis of the orifice through the locking member aligns with the central axis of the pathway through the housing, and a second position wherein the second end of the locking member is spaced from the distal end of the other tab and the central axis of the locking member is misaligned with the central axis of the pathway through the housing,
- (4) whereby the catheter movement control device permits withdrawal of the catheter from the packaging through the passageway in the housing, while inhibiting return of a withdrawn length of the catheter into the packaging.

7. The packaged intermittent urinary catheter of claim 6 wherein the packaging is flexible packaging.

8. The packaged intermittent urinary catheter of claim 6 wherein the locking member is planar.

9. The packaged intermittent urinary catheter of claim 6 wherein the locking member is hingedly attached to the housing by a live hinge.

10. The packaged intermittent urinary catheter of claim 6 wherein the orifice includes a plurality of inwardly projecting teeth.

\* \* \* \* \*